United States Patent [19]

Babler

[11] Patent Number: 5,107,030

[45] Date of Patent: Apr. 21, 1992

[54] METHOD OF MAKING 2,7-DIMETHYL-2,4,6-OCTATRIENEDIAL AND DERIVATIVES THEREOF

[75] Inventor: James H. Babler, Chicago, Ill.

[73] Assignee: Loyola University of Chicago, Chicago, Ill.

[21] Appl. No.: 661,722

[22] Filed: Mar. 4, 1991

[51] Int. Cl.$^5$ .................. C07C 47/21; C07C 45/00
[52] U.S. Cl. ............................ 568/494; 560/195; 568/449; 568/484
[58] Field of Search ............... 568/494, 484, 449, 485, 568/495

[56] References Cited

U.S. PATENT DOCUMENTS

| 2,948,748 | 8/1960 | Guex et al. | 568/494 |
| 3,009,921 | 11/1961 | Stilz et al. | 568/494 |
| 3,577,464 | 5/1971 | Gutmann et al. | 568/494 |

FOREIGN PATENT DOCUMENTS

| 1092472 | 11/1960 | Fed. Rep. of Germany | 568/494 |
| 1518602 | 5/1969 | Fed. Rep. of Germany | 568/494 |
| 1503429 | 11/1967 | France | 568/494 |
| 756896 | 9/1956 | United Kingdom | 568/494 |

OTHER PUBLICATIONS

O. Isler, *Carotenoids*, pp. 431–437.
Horst Pommer et al., *Industrial Applications of the Wittig Reaction*, vol. 109 (1983) pp. 165–188.
H. Pommer, *Synthesen in der Carotinoid-Reihe*, Angew. Chem/72.Jahrg.1960/Nr. 23.
Carsky et al., Liebigs Ann. Chem. (1980) 291–304.
*The Chemist's Companion*, Drying Agents, pp. 445–447.
Shyam K. Gupta, *J. Org. Chem.*, vol. 41, No. 15 (1976).

*Primary Examiner*—Werren B. Lone
*Attorney, Agent, or Firm*—Marshall, O'Toole, Gerstein, Murray & Bicknell

[57] ABSTRACT

The present invention is an improved method to prepare 2,7-dimethyl-2,4,6-octatrienedial and related derivative compounds. This method of making 2,7-dimethyl-2,4,6-octatrienedial and derivatives thereof includes reacting 2-butenyl-bisphosphonic acid tetraalkyl ester and at least two equivalents of protected pyruvic aldehyde derivative in a nonpolar organic solvent in the presence of an alkali metal hydroxide. Compounds prepared by this invention are useful intermediates in the preparation of carotenoids.

13 Claims, No Drawings

METHOD OF MAKING 2,7-DIMETHYL-2,4,6-OCTATRIENEDIAL AND DERIVATIVES THEREOF

BACKGROUND

The present invention relates to an improved method of making 2,7-dimethyl-2,4,6-octatrienedial and related derivatives. Specifically, this invention describes a method for reacting a readily available four carbon atom bisphosphonate with two equivalents of both a pyruvic aldehyde derivative and a powdered alkali metal hydroxide to give the desired dimethyloctatrienedial in high yields.

The group of naturally occurring compounds commonly known as carotenoids have found increasing uses in the coloration of foodstuffs and in animal feedstocks. The carotenoids include terpenes made of forty carbon atoms. For example, beta-carotene, illustrated by Formula I, is a representative compound of this class.

Formula I

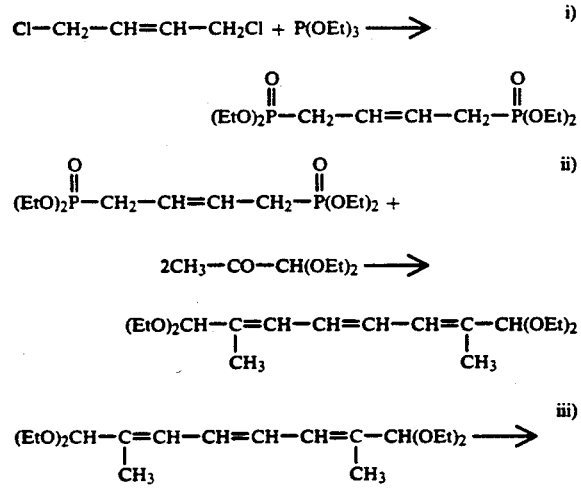

Published syntheses of beta-carotene have advantageously used the symmetry of the compound to develop convergent synthetic schemes to make the compound. In particular, the ten carbon atom fragment in the center of the compound (the fragment included within the dashed lines as illustrated in Formula I) has been used in known synthetic schemes. Various methods for preparing this ten carbon atom fragment are described by Isler, *Carotenoids*, Birkhauser-Verlag, 431–436 (1971) and by Pommer et al, "Industrial Applications of the Wittig Reaction," *Topics in Current Chemistry*, 109: 165–188 (1983).

A known industrial preparation of the ten carbon fragment 2,7-dimethyl-2,4,6-octatrienedial was developed by BASF. The BASF process described by Pommer, *Angew. Chem.*, 72: 911–915 (1960) is schematically outlined in Scheme 1:

Scheme 1

Cl—CH$_2$—CH=CH—CH$_2$Cl + P(OEt)$_3$ $\longrightarrow$  i)

$$(EtO)_2\overset{O}{\overset{\|}{P}}-CH_2-CH=CH-CH_2-\overset{O}{\overset{\|}{P}}(OEt)_2$$

$(EtO)_2\overset{O}{\overset{\|}{P}}-CH_2-CH=CH-CH_2-\overset{O}{\overset{\|}{P}}(OEt)_2$ +   ii)

2CH$_3$—CO—CH(OEt)$_2$ $\longrightarrow$ (EtO)$_2$CH—C=CH—CH=CH—CH=C—CH(OEt)$_2$
  |                                   |
  CH$_3$                              CH$_3$ (EtO)$_2$CH—C=CH—CH=CH—CH=C—CH(OEt)$_2$ $\longrightarrow$   iii)
  |                                   |
  CH$_3$                              CH$_3$ -continued
Scheme 1

OCH—C=CH—CH=CH—CH=C—CHO
  |                       |
  CH$_3$                  CH$_3$

This sequence has also been described in German Patent 1,092,472, Nov. 10, 1960. The abstract of this patent in *Chemical Abstracts*, 56: 413d (1962) describes the reaction conditions used for the sequence illustrated in Scheme 1 as reacting the bisphosphonate with an excess of the carbonyl compound in the solvent dimethylformamide in the presence of sodium methoxide. As reported, the reaction of the bisphosphonate (53 g) with an excess of the diethoxy pyruvaldehyde derivative (88 g) gave the desired octatrienedial (14.7 g), a yield of about 55%. The overall low efficiency of this reported sequence, use of a less desirable solvent, and use of an excess of the protected aldehyde reagent indicate a need for a more efficient process employing reagents and solvents which are easier to handle, dispose of and recycle when used in a larger scale process.

The undesirable, low yields associated with the reaction of carbonyl compounds with this same bisphosphonate reagent are described by Carsky et al., *Liebig's Annalen der Chemie*, 291–304 (1980). Reported yields of the reactions of various carbonyl compounds with this bisphosphonate were generally low ranging from about 20–25%. The described reaction conditions reacted the bisphosphonate with the carbonyl compounds in 1,2-dimethoxyethane in the presence of potassium tert-butoxide. The generally low yields provided by these conditions suggest that using aprotic solvents and alkoxide bases does not provide an efficient, economical synthetic route to 2,7-dimethyl-2,4,6-octatrienedial. Attempts to duplicate similar methods also were found to be unsatisfactory due to poor yields and/or complex reaction mixtures which may require potentially costly and complex purification schemes if used in large-scale commercial preparations.

The present invention provides for the formation of 2,7-dimethyl-2,4,6-octatrienedial using inexpensive, recyclable nonpolar solvents and an alkali metal hydroxide. It was unexpected that the use of a virtually insoluble hydroxide base in a nonpolar solvent would provide both an increase in the overall yield of the coupling reaction between the bisphosphonate and the carbonyl compound and a decrease in the formation of undesired by-products.

The observed increase in yield is certainly unpredicted because the use of a hydroxide base in nonpolar solvents generally must be performed under phase-transfer catalysis conditions. When the coupling reaction is done under phase-transfer catalysis conditions, typically use of a nonpolar solvent, saturated aqueous hydroxide and a catalytic amount of a quaternary ammonium salt, the coupling reaction was found to be less satisfactory than when powdered hydroxide alone was used. It was also observed that the use of an alkoxide base, which is a more soluble base in nonpolar solvents, was less satisfactory than use of powdered hydroxide alone. The unpredicted increased overall yield and decreased formation of by-products provided by the present method is an important feature of this invention.

SUMMARY OF THE INVENTION

The present invention provides an improved method for making 2,7-dimethyl-2,4,6-octatriendial or a derivative thereof by reacting 2-butenyl-1,4-bisphosphonic acid tetraalkyl ester and two equivalents of a protected pyruvic aldehyde derivative and then removing the aldehyde protecting group. The present method includes the steps of forming a reaction mixture at a temperature of about 0°-25° C. in an essentially water-free, nonpolar organic solvent of the reagents:

i)

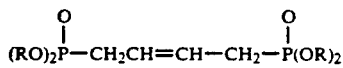

where R is $C_1$-$C_4$ alkyl;

ii) $CH_3CO-CH=Z$ where $CH=Z$ is a protected aldehyde; and iii) at least two equivalents of a solid alkali metal hydroxide; and isolating

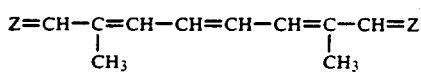

from said reaction mixture. The aldehyde protecting groups Z may be readily removed to provide the desired dialdehyde.

The foregoing method is outlined in Scheme 2.

Scheme 2

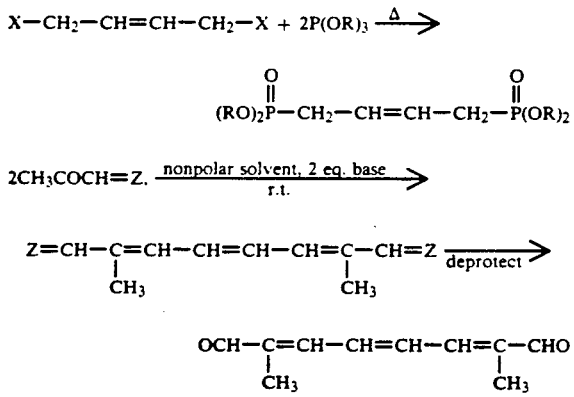

In Scheme 2, X is either chlorine or bromine and the phosphite reagent $P(OR)_3$, includes compounds where R may be methyl, ethyl, propyl, isopropyl, butyl, isobutyl, or sec-butyl. Similarly, the carbonyl reagent represented by $CH_3-CO-CH=Z$ includes a protected aldehyde equivalent, $-CH=Z$, which readily gives the aldehyde functionality upon deprotection. Preferred protecting groups include the acetal derivative of pyruvic aldehyde represented by the formula $CH_3-CO-CH(OR^1)_2$ where $=Z$ is $-(OR^1)_2$ and where $R^1$ is $C_1$-$C_4$ alkyl such as methyl, ethyl, propyl, isopropyl, butyl, isobutyl, sec-butyl or tert-butyl, preferably methyl or where $=Z$ is the cyclic acetal of pyruvic aldehyde and the carbonyl compound is represented by the formula

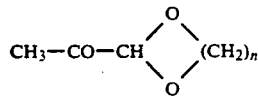

where n is the integer 2 or 3. As such, either the five membered or six membered cyclic acetals are included. Other suitable pyruvic aldehyde derivatives are described by Gupta, *J. Org. Chem.*, 41: 2642–2645 (1976).

When $-CH=Z$ is either the dialkoxy or the cyclic acetal derivative, the protecting group is readily removed by reacting the protected aldehyde under aqueous acidic conditions in a suitable solvent which readily hydrolyzes the dialkoxy or cyclic acetal derivative and gives the free dialdehyde compound.

Preferably, the reaction of the illustrated phosphonic acid derivative with two equivalents of the carbonyl compound occurs in an essentially water-free, nonpolar solvent such as toluene, xylene, benzene, cyclohexane, hexane, heptane or mixtures therefore. Alternative solvents or cosolvents include diisopropylamine, diisopropyl ether, triethylamine, chlorobenzene or tetrahydrofuran. The reaction is performed under conditions which exclude atmospheric moisture and carbon dioxide. The use of a hydroxide base is essential.

Although the solubility of alkali metal hydroxides in nonpolar solvents of the type set out above is known to be very low, the reaction occurs efficiently under such conditions. Potassium or sodium hydroxide are preferred alkali metal hydroxides. The hydroxide base is generally ground to a powder before use in the present reaction. Although at least two equivalents of hydroxide base are required, an amount of base in excess of two equivalents is acceptable. It is believed that any excess base may act as a drying agent to remove the two equivalents of water which are generated by the above illustrated coupling reaction. Other well known drying agents may optionally be added to the reaction mixture. Any suitable drying agent may be used, such as anhydrous potassium carbonate or other insoluble drying agents. Suitable drying agents are described in *The Chemist's Companion* on pp 445–447.

In sum, the method of the present invention provides an efficient process to couple bisphosphonates and carbonyl compounds. The high yield of the coupling reaction, typically 70–90%, is a significant improvement over known coupling processes. In particular, the coupling of 2-butenyl-1,4-bisphosphonic acid tetraalkyl ester with two equivalents of pyruvic aldehyde dimethyl acetal to give tetramethoxy octatriene in greater than 80% yield is a significant improvement to other known processes.

The formulas illustrated in Scheme 2 are not intended to depict any stereochemistry. Any mixture of cis and trans isomers may be used in subsequent carotenoid synthesis and, if needed, known carbon-carbon double bond isomerization methods may be used to give a specific, desired stereoisomer.

Detailed Description

The following examples illustrate specific embodiments of the practice of method of the present invention. Important starting reagents or materials prepared according to known procedures are described in Examples I, II and IX. The coupling reaction of the bisphosphonate and the carbonyl compound in a nonpolar solvent is described in Examples III, IV, V, VI, VII, X, XV, XVII, XIX, XX, XXI, XXII and XXIII. The removal of the methoxy groups which are used to protect the aldehyde functionality as the acetal is described in Example XXVI. The use of additional dehydrating agents is described in Example VIII. Comparative reaction conditions which are inferior to the method of the present invention are described in Examples XI, XII, XIII, XIV, XVI, XVIII, XXIV, XXV.

In the examples, percent yields indicate the material recovered after work-up of the specific reaction mixtures. The purity of the desired bisacetal in the recovered material was readily determined using NMR spectroscopy. Specifically, the desired compound,

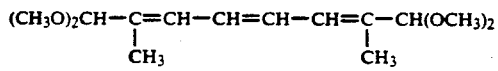

has a relatively simple, distinct NMR spectra (δ:1.8, s 6H, =C—CH₃; 3.37 overlapping s, 6H, CH₃O—; 4.63, s, 2H, (CH₃O)₂ CH—; and 6.5, m, 4H, =CH—. The presence of impurities in the recovered material can be readily seen by the addition of extra peaks in an NMR spectra of the crude recovered material.

EXAMPLE I

Preparation of 2-Butenyl-1,4-bisphosphonic Acid, Tetraethyl Ester

A solution of 2.00 mL (18.9 mmoles) of trans-1,4-dichloro-2-butene in 3.00 mL (17.5 mmoles) of triethyl phosphite was slowly added dropwise over a period of twenty-five minutes to a heated vessel containing 5.00 mL (29.2 mmoles) of triethyl phosphite which was maintained at a temperature of approximately 140° C. (external oil bath temperature). This mixture was subsequently heated at 140° C. for an additional twelve hours, during which time ethyl chloride was continuously distilled out of the reaction vessel. At that point, the external oil bath temperature was raised to 180° C. to distill over as much of the reamining triethyl phosphite as possible. The desired product was then obtained by fractional distillation under reduced pressure, affording 5.40 g (87.5% yield) of the named bisphosphonate having a boiling point of about 161°-184° C. (bath temperature, 0.25 mm).

A 93.5% yield of this same bisphosphonate has been obtained in a large-scale synthesis, reported in French patent 1,503,429 (Nov. 24, 1967) and *Chem. Abstracts*, 69: 96, 874m (1968).

EXAMPLE II

Preparation of 2-Butenyl-1,4-bisphosphonic Acid, Tetraisopropyl Ester

A solution of 2.00 mL (18.9 mmoles) of trans-1,4-dichloro-2-butene (technical grade, purchased from Aldrich Chemical Company, Milwaukee, Wis.) in 5.00 mL (20.3 mmoles) of triisopropyl phosphite was added dropwise slowly over thirty minutes to a heated vessel containing 7.00 mL (28.4 mmoles) of triisopropyl phosphite which was maintained at a temperature of approximately 140° C. (external oil bath temperature). This mixture was subsequently heated at 140° C. for an additional ninety minutes, after which it was heated at 160° C. for eighteen hours, during which time isopropyl chloride was continuously distilled out of the reaction vessel. The desired product was then obtained by fractional distillation under reduced pressure, affording 6.15 g (85% yield) of the named bisphosphonate having a boiling point of about 163°-178° C. (bath temperature, 0.25 mm).

EXAMPLE III

Preparation of 1,1,8,8-Tetramethoxy-2,7-dimethyl-2,4,6-octatriene Using Sodium Hydroxide in a Mixture of Toluene and Cyclohexane To a solution of 332 mg (1.01 mmole) of 2-butenyl-1,4-bisphosphonic acid, tetraethyl ester (produced in accordance with Example I) and 0.25 mL (2.07 mmoles) of pyruvic aldehyde dimethyl acetal (available from Aldrich Chemical Co., Milwaukee, Wis.) in 2.00 mL of a 1:1 (v/v) mixture of toluene:cyclohexane was added 592 mg (14.8 mmoles) of sodium hydroxide (A.C.S. reagent-grade sodium hydroxide pellets, finely powdered using a mortar and pestle). This mixture, protected from atmospheric moisture and carbon dioxide, was subsequently stirred at room temperature for four hours. In order to isolate the product, the mixture was cooled to a temperature of approximately 15° C. by use of an external cold water bath, and 10 mL of 10% aqueous sodium chloride was added to the mixture to dissolve excess sodium hydroxide and other salts. After dilution of this mixture with 20 mL of 1:1 (v/v) pentane:ether, the layers were separated and the organic layer was washed in successive order with 10% aqueous sodium chloride (20 mL) and saturated brine (20 mL). The washed organic layer was then dried over anhydrous sodium sulfate and filtered. Removal of the volatile organic solvents by evaporation at reduced pressure and subsequent pumping under high vacuum (0.20 mm) to remove traces of residual toluene afforded 173 mg (67% yield) of the desired bisacetal, the identity and purity of which were ascertained by proton NMR analysis.

In this example, as well as in examples conducted using other nonpolar solvents, the major impurities contaminating the desired product included unreacted pyruvic aldehyde dimethyl acetal (generally 5% or less) and trace amounts of a material independently shown to be derived from self-condensation of this ketone. Use of more polar solvents for this reaction (as described below) or substitution of alkoxide bases for the hydroxide significantly decreased both the yield and purity of the desired bisacetal and resulted in the formation of several unidentified by-products not observed when the reaction was conducted in nonpolar solvents with hydroxide as the base.

In larger industrial-scale processes, various alternative isolation procedures are suitable. For example, prior to addition of the aqueous sodium chloride to the reaction mixture and subsequent isolation of the product, the nonpolar organic solvents may be removed by distillation (at reduced pressure, if necessary) and recycled. The desired bisacetal may then be separated from the residual mixture (after addition of water, if necessary) by continuous extraction with a suitable solvent such as heptane.

EXAMPLE IV

Preparation of
1,1,8,8-Tetramethoxy-2,7-dimethyl-2,4,6-octatriene
Using Potassium Hydroxide in a Mixture of Toluene
and Cyclohexane The reaction was conducted in the manner described in the procedure of Example III using the following reagents: 324 mg (0.99 mmole) of 2-butenyl-1,4-bisphosphonic acid, tetraethyl ester (produced in accordance with Example I), 0.25 mL (2.07 mmoles) of pyruvic aldehyde dimethyl acetal, 1.00 mL of toluene, 1.00 mL of cyclohexane, and 683 mg (10.3 mmoles) of powdered 85% potassium hydroxide (85% KOH pellets, finely powdered using a mortar and pestle). Isolation of the product as described in the procedure of Example III afforded 172 mg (68% yield) of the desired bisacetal. A similar experiment in which potassium hydroxide was replaced by anhydrous potassium carbonate (853 mg, 6.2 mmoles) led to the recovery of starting materials, with no bisacetal formation.

EXAMPLE V

Preparation of
1,1,8,8-Tetramethoxy-2,7-dimethyl-2,4,6-octatriene
Using Solid Potassium Hydroxide at 0° C.

To a solution of 325 mg (0.99 mmole) of 2-butenyl-1,4-bisphosphonic acid, tetraethyl ester (produced in accordance with Example I) and 0.25 mL (2.07 mmoles) of pyruvic aldehyde dimethyl acetal in 2.00 mL of a 1:1 (v/v) mixture of toluene:cyclohexane, protected from atmospheric moisture and maintained at a temperature of 0° C. by use of an external ice water bath, was added 620 mg (9.4 mmoles) of powdered 85% potassium hydroxide. This mixture was stirred at 0° C. for six and one-half hours, after which it was diluted with 10 mL of 10% aqueous sodium chloride. The product was subsequently isolated as described in the procedure of Example III, affording 181 mg (71% yield) of the desired bisacetal.

EXAMPLE VI

Use of 2-Butenyl-1,4-bisphosphonic Acid,
Tetraisopropyl Ester to Prepare
1,1,8,8-Tetramethoxy-2,7-dimethyl-2,4,6-octatriene To a solution of 378 mg (0.98 mmole) of 2-butenyl-1,4-bisphosphonic acid, tetraisopropyl ester (produced in accordance with Example II) and 0.25 mL (2.07 mmoles) of pyruvic aldehyde dimethyl acetal in 2.00 mL of a 1:1 (v/v) mixture of toluene:cyclohexane was added 572 mg (14.3 mmoles) of powdered sodium hydroxide. This mixture, protected from atmospheric moisture, was subsequently stirred at room temperature for four hours. Isolation of the product as described in the procedure of Example III afforded 205 mg (82% yield) of the desired bisacetal.

EXAMPLE VII

Preparation of 1,1,8,8-Tetramethoxy-2,7-dimethyl-2,4,6-octatriene Using Only a Small Excess of Sodium Hydroxide The reaction was conducted in the manner described in the procedure of Example III using the following reagents: 319 mg (0.97 mmole) of 2-butenyl-1,4-bisphosphonic acid, tetraethyl ester (produced in accordance with Example I), 0.25 mL (2.07 mmoles) of pyruvic aldehyde dimethyl acetal, 1.00 mL of toluene, 1.00 mL of cyclohexane, and 122 mg (3.05 mmoles) of powdered sodium hydroxide. Isolation of the product as described in the procedure of Example III afforded 166 mg (67% yield) of crude bisacetal product, substantially less pure by NMR and IR analysis than the product described in Example III. In particular, the isolated product contained more by-products independently shown to be derived from self-condensation of pyruvic aldehyde dimethyl acetal. Such results are consistent with those obtained when the preparation of the desired bisacetal was conducted using 72% (w/v) aqueous sodium hydroxide in lieu of powdered sodium hydroxide (Example XII) and indicates the desirability of a water-scavenger (i.e., excess powdered hydroxide or other drying agent as described in Example VIII) in the reaction mixture in order to maximize the yield of 1,1,8,8-tetramethoxy-2,7-dimethyl-2,4,6-octatriene.

EXAMPLE VIII

Preparation of
1,1,8,8-Tetramethoxy-2,7-dimethyl-2,4,6-octatriene
Using a Drying Agent Other Than Hydroxide The reaction was conducted in the manner described in the procedure of Example III using the following reagents: 318 mg (0.97 mmole) of 2-butenyl-1,4-bisphosphonic acid, tetraethyl ester (produced in accordance with Example I), 0.25 mL (2.07 mmoles) of pyruvic aldehyde dimethyl acetal, 1.00 mL of toluene, 1.00 mL of cyclohexane, 992 mg (7.18 mmoles) of anhydrous potassium carbonate, and 121 mg (3.02 mmoles) of powdered sodium hydroxide. Isolation of the product as described in the procedure of Example III afforded 197 mg (79% yield) of the desired bisacetal. For other suitable drying agents (e.g., activated molecular sieves) see: Gordon et al., *The Chemist's Companion*, pages 445–447 (1972).

EXAMPLE IX

Preparation of 2-Acetyl-1,3-dioxane

A mixture of 3.81 g of 1,3-dihydroxyacetone dimer (available from Aldrich Chemical Co., Milwaukee, Wis.) and 308 mg of Amberlyst-15 ion-exchange resin (Aldrich Chemical Co., Milwaukee, Wis.) in 10 mL of 1,3-propanediol was stirred for four hours at a temperature of about 105° C. (external oil bath temperature) and protected from atmospheric moisture. After cooling the mixture to room temperature, it was filtered through a plug of glass wool into a separatory funnel containing 50 mL of 10% aqueous sodium chloride; and the product was isolated by extraction with dichloromethane (2×15 mL portions). The combined dichloromethane extracts were washed with saturated brine (30 mL), then dried over anhydrous sodium sulfate and filtered. Removal of dichloromethane by evaporation at reduced pressure, followed by evaporative distillation (bath temperature: 72°–91° C., 2.5 mm) afforded 2.92 g (53% yield) of the desired product, greater than 98% pure as shown by gas chromatographic analysis. The title compound, 2-acetyl-1,3-dioxane, has been previously prepared in a similar manner by S. K. Gupta, *J. Org. Chem.*, 41, 2642 (1976).

EXAMPLE X

Preparation of 2,7-Bis(1,3-dioxan-2-yl)-2,4,6-octatriene

The reaction was conducted in the manner described in the procedure of Example III using the following reagents: 322 mg (0.98 mmole) of 2-butenyl-1,4-bisphosphonic acid, tetraethyl ester (produced in accordance with Example I), 278 mg (2.14 mmoles) of 2-acetyl-1,3-dioxane (produced in accordance with Example IX), 2.00 mL of toluene, and 586 mg (14.6 mmoles) of powdered sodium hydroxide. Isolation of the product as described in the procedure of Example III afforded 172 mg (63% yield) of the desired bisacetal.

EXAMPLE XI

Preparation of
1,1,8,8-Tetramethoxy-2,7-dimethyl-2,4,6-octatriene
Using Phase-Transfer Catalysis Conditions To a mixture of 321 mg (0.98 mmole) of 2-butenyl-1,4-bisphosphonic acid, tetraethyl ester (produced in accordance with Example I), pyruvic aldehyde dimethyl acetal (0.25 mL, 2.07 mmoles), and 44 mg of tetrabutylammonium hydrogen sulfate (0.13 mmole) in 2.00 mL of cyclohexane was added 2.00 mL of 50% (weight/volume) aqueous sodium hydroxide (prepared by dissolving 5 g of sodium hydroxide pellets in 7.5 mL of water). This mixture, protected from atmospheric moisture and carbon dioxide, was subsequently stirred at room temperature for five and one-half hours. In order to isolate the product, the mixture was cooled to a temperature of approximately 15° C. by use of an external cold water bath, and 10 mL of water was added to the flask. After dilution of this mixture with 20 mL of 1:1 (volume/volume) pentane:ether, the layers were separated and the organic layer was washed with saturated brine (20 mL). The washed organic layer was then dried over anhydrous sodium sulfate and filtered. Removal of the volatile organic solvents by evaporation at reduced pressure afforded 64 mg (25% yield) of very crude bisacetal, less than 50% pure by NMR analysis. A similar experiment was conducted using a more concentrated aqueous solution of sodium hydroxide (72% weight/volume) and afforded a significantly purer sample of the desired bisacetal in 42% yield. However, such results are considerably inferior to those obtained using powdered sodium hydroxide under essentially anhydrous conditions.

EXAMPLE XII

Preparation of
1,1,8,8-Tetramethoxy-2,7-dimethyl-2,4,6-octatriene
Using Concentrated Aqueous Sodium Hydroxide In the
Absence of a Phase-Transfer Catalyst To a mixture of 324 mg (0.99 mmole) of 2-butenyl-1,4-bisphosphonic acid, tetraethyl ester (produced in accordance with Example I) and 0.25 mL (2.07 mmoles) of pyruvic aldehyde dimethyl acetal in 2.00 mL of cyclohexane was added 2.00 mL of 72% (weight/volume) aqueous sodium hydroxide (prepared by dissolving 7.2 g of sodium hydroxide pellets in 6.5 mL of water). This mixture, protected from atmospheric moisture and carbon dioxide, was subsequently stirred at room temperature for four hours. Isolation of the product as described in the procedure of Example XI afforded 145 mg (57% yield) of the desired bisacetal, shown by NMR analysis to be less pure than the product obtained using sodium hydroxide (without addition of water) as a base with nonpolar organic solvents. Similar results were obtained when this experiment was conducted using 2.00 mL of a 1:1 (v/v) mixture of toluene:cyclohexane as the organic solvent.

EXAMPLE XIII

Preparation of
1,1,8,8-Tetramethoxy-2,7-dimethyl-2,4,6-octatriene in
the Absence of an Organic Solvent To a mixture of 330 mg (1.01 mmoles) of 2-butenyl-1,4-bisphosphonic acid, tetraethyl ester (produced in accordance with Example I) and 0.25 mL (2.07 mmoles) of pyruvic aldehyde dimethyl acetal was added 589 mg. (14.7 mmoles) of powdered sodium hydroxide. This mixture, protected from atmospheric moisture and carbon dioxide, was subsequently stirred at room temperature for one hour at which point it became too viscous to stir and then was allowed to stand at room temperature for an additional one and one-half hours. Isolation of the product as described in the procedure of Example III afforded 164 mg (63% yield) of crude bisacetal, less than 50% pure by NMR analysis. A significant amount of self-condensation products derived from pyruvic aldehyde dimethyl acetal contaminated this bisacetal, along with other unidentified by-products.

EXAMPLE XIV

Preparation of
1,1,8,8-Tetramethoxy-2,7-dimethyl-2,4,6-octatriene
Using Dimethyl Sulfoxide as the Solvent The reaction was conducted in the manner described in the procedure of Example III using the following reagents: 319 mg (0.97 mmole) of 2-butenyl-1,4-bisphosphonic acid, tetraethyl ester (produced in accordance with Example I), 0.25 mL (2.07 mmoles) of pyruvic aldehyde dimethyl acetal, 2.00 mL of dimethyl sulfoxide (spectrophotometric-grade, purchased from Aldrich Chemical Co., Milwaukee, Wis.), and 568 mg. (14.2 mmoles) of powdered sodium hydroxide. Isolation of the product as described in the procedure of Example III (with the addition of using three washes of the organic layer with 10% aqueous sodium chloride to ensure removal of dimethyl sulfoxide) afforded 55 mg (22% yield) of the desired bisacetal. An identical experiment was conducted using 1-methyl-2-pyrrolidinone as the organic solvent and afforded the bisacetal in only 25% yield. Polar aprotic solvents are, therefore, not preferred solvents in this reaction, although Examples XVIII and XIX illustrate the feasibility of using polar aprotic solvents as cosolvents with a nonpolar solvent.

EXAMPLE XV

Preparation of
1,1,8,8-Tetramethoxy-2,7-dimethyl-2,4,6-octatriene
Using Cyclohexane as the Solvent The reaction was conducted in the manner described in the procedure of Example III using the following reagents: 324 mg (0.99 mmole) of 2-butenyl-1,4-bisphosphonic acid, tetraethyl ester (produced in accordance with Example I), 0.25 mL (2.07 mmoles) of pyruvic aldehyde dimethyl acetal, 2.00 mL of cyclohexane, and 534 mg (13.3 mmoles) of powdered sodium hydroxide. Isolation of the product as described in the procedure of Example III afforded 158 mg (62% yield) of the desired bisacetal.

EXAMPLE XVI

Preparation of
1,1,8,8-Tetramethoxy-2,7-dimethyl-2,4,6-octatriene Using 10:1 (volume/volume) Cyclohexane: Ethyl Alcohol as the Solvent The reaction was conducted in the manner described in the procedure of Example III using the following reagents: 331 mg (1.01 mmoles) of 2-butenyl-1,4-bisphosphonic acid, tetraethyl ester (produced in accordance with Example I), 0.25 mL (2.07 mmoles) of pyruvic aldehyde dimethyl acetal, 2.00 mL of cyclohexane, 0.20 mL of absolute ethyl alcohol, and 574 mg (14.3 mmoles) of powdered sodium hydroxide. Isolation of the product as described in the procedure of Example III afforded 106 mg (41% yield) of crude bisacetal, shown by infrared and proton NMR analysis to be significantly less pure than the product obtained in Example XV.

EXAMPLE XVII

Preparation of
1,1,8,8-Tetramethoxy-2,7-dimethyl-2,4,6-octatriene Using Hexane as the Solvent The reaction was conducted in the manner described in the procedure of Example III using the following reagents: 326 mg (0.99 mmole) of 2-butenyl-1,4-bisphosphonic acid, tetraethyl ester (produced in accordance with Example I), 0.25 mL (2.07 mmoles) of pyruvic aldehyde dimethyl acetal, 2.00 mL of hexane (in which the bisphosphonate is only slightly soluble), and 564 mg (14.1 mmoles) of powdered sodium hydroxide. Isolation of the product as described in the procedure of Example III afforded 145 mg (57% yield) of the desired bisacetal. The diminished yield in this experiment may be due to the low solubility of the starting bisphosphonate in hexane.

EXAMPLE XVIII

Preparation of
1,1,8,8-Tetramethoxy-2,7-dimethyl-2,4,6-octatriene Using N,N-dimethylformamide as the Solvent The reaction was conducted in the manner described in the procedure of Example III using a reaction time of five hours and the following reagents: 323 mg (0.98 mmole) of 2-butenyl-1,4-bisphosphonic acid, tetraethyl ester (produced in accordance with Example I), 0.25 mL (2.07 mmoles) of pyruvic aldehyde dimethyl acetal, 2.00 mL of dimethylformamide (spectrophotometric-grade, purchased from Aldrich Chemical Co., Milwaukee, Wis.), and 575 mg (14.4 mmoles) of powdered sodium hydroxide. Isolation of the product as described in the procedure of Example III (with the addition of using three washes of the organic layer with 10% aqueous sodium chloride to ensure removal of dimethylformamide) afforded 68 mg (27% yield) of the desired bisacetal.

EXAMPLE XIX

Preparation of
1,1,8,8-Tetramethoxy-2,7-dimethyl-2,4,6-octatriene Using a Mixture of Toluene and Dimethylformamide as the Solvent The reaction was conducted in the manner described in the procedure of Example III using a reaction time of five hours and the following reagents: 320 mg (0.97 mmole) of 2-butenyl-1,4-bisphosphonic acid, tetraethyl ester (produced in accordance with Example I), 0.25 mL (2.07 mmoles) of pyruvic aldehyde dimethyl acetal, 1.00 mL of dimethylformamide (spectrophotometric-grade, purchased from Aldrich Chemical Co., Milwaukee, Wis.), 1.00 mL of toluene, and 574 mg (14.3 mmoles) of powdered sodium hydroxide. Isolation of the product as described in the procedure of Example III (with the addition of using three washes of the organic layer with 10% aqueous sodium chloride to ensure removal of dimethylformamide) afforded 128 mg (51% yield) of the desired bisacetal.

EXAMPLE XX

Preparation of
1,1,8,8-Tetramethoxy-2,7-dimethyl-2,4,6-octatriene Using Tetrahydrofuran as the Solvent The reaction was conducted in the manner described in the procedure of Example III using the following reagents: 328 mg (1.00 mmole) of 2-butenyl-1,4-bisphosphonic acid, tetraethyl ester (produced in accordance with Example I) 0.25 mL (2.07 mmoles) of pyruvic aldehyde dimethyl acetal, 2.00 mL of anhydrous tetrahydrofuran, and 580 mg (14.5 mmoles) of powdered sodium hydroxide. Isolation of the product as described in the procedure of Example III afforded 145 mg (57% yield) of the desired bisacetal. Similar results were obtained when this experiment was conducted using 2.00 mL of diisopropyl ether as the organic solvent.

EXAMPLE XXI

Preparation of
1,1,8,8-Tetramethoxy-2,7-dimethyl-2,4,6-octatriene Using Triethylamine as the Solvent The reaction was conducted in the manner described in the procedure of Example III using the following reagents: 323 mg (0.98 mmole) of 2-butenyl-1,4-bisphosphonic acid, tetraethyl ester (produced in accordance with Example I), 0.25 mL (2.07 mmoles) of pyruvic aldehyde dimethyl acetal, 2.00 mL of triethylamine, and 578 mg (14.4 mmoles) of powdered sodium hydroxide. Isolation of the products as described in the procedure of Example III afforded 144 mg (57% yield) of the desired bisacetal. A similar experiment in which sodium hydroxide was not added to the reaction mixture led to the recovery of starting materials, with no bisacetal formation.

EXAMPLE XXII

Preparation of
1,1,8,8-Tetramethoxy-2,7-dimethyl-2,4,6-octatriene Using Diisopropylamine as the Solvent The reaction was conducted in the manner described in the procedure of Example III using a reaction time of five hours and the following reagents: 318 mg (0.97 mmole) of 2-butenyl-1,4-bisphosphonic acid, tetraethyl ester (produced in accordance with Example I), 0.25 mL (2.07 mmoles) of pyruvic aldehyde dimethyl acetal, 2.00 mL of diisopropylamine, and 561 mg (14.0 mmoles) of powdered sodium hydroxide. Isolation of the product as described in the procedure of Example III afforded 149 mg (60% yield) of the desired bisacetal, shown by reverse phase high pressure liquid chromatography to be greater than 95% pure (300 mm×4.6 mm I.D. column packed with octadecylsilane on spherisorb S100DS, eluted with 80% methanol:20% water

EXAMPLE XXIII

Preparation of
1,1,8,8-Tetramethoxy-2,7-dimethyl-2,4,6-octatriene
Using Chlorobenzene as the Solvent The reaction was conducted in the manner described in the procedure of Example III using the following reagents: 330 mg (1.01 mmoles) of 2-butenyl-1,4-bisphosphonic acid, tetraethyl ester (produced in accordance with Example I), 0.25 mL (2.07 mmoles) of pyruvic aldehyde dimethyl acetal, 2.00 mL of chlorobenzene, and 584 mg (14.6 mmoles) of powdered sodium hydroxide. Isolation of the product as described in the procedure of Example III afforded 157 mg (61% yield) of the desired bisacetal after removal of the last traces of chlorobenzene.

EXAMPLE XXIV

Preparation of
1,1,8,8-Tetramethoxy-2,7-dimethyl-2,4,6-octatriene
Using Alkoxide Bases The reaction was conducted in the manner described in the procedure of Example III using the following reagents: 322 mg (0.98 mmole) of 2-butenyl-1,4-bisphosphonic acid, tetraethyl ester (produced in accordance with Example I), 0.25 mL (2.07 mmoles) of pyruvic aldehyde dimethyl acetal, 2.00 mL of cyclohexane, and 480 mg (8.89 mmoles) of powdered sodium methoxide. Isolation of the product as described in the procedure of Example III afforded 125 mg of material, shown by infrared and proton NMR analysis to be a complex mixture of components containing a minor amount of the desired bisacetal. Use of sodium ethoxide powder (8.8 mmoles) as the base in a solvent mixture of toluene-cyclohexane also resulted in the formation of a complex mixture containing only a trace of the desired bisacetal.

EXAMPLE XXV

Preparation of
1,1,8,8-Tetramethoxy-2,7-dimethyl-2,4,6-octatriene
Using Potassium tert-Butoxide as the Base To a solution of 312 mg (0.95 mmole) of 2-butenyl-1,4-bisphosphonic acid, tetraethyl ester (produced in accordance with Example I) and 0.25 mL (2.07 mmoles) of pyruvic aldehyde dimethyl acetal in 3.25 mL of 12:1 (v/v) anhydrous tetrahydrofuran:dimethyl sulfoxide, protected from atmospheric moisture and maintained at a temperature of approximately 5° C. by use of an external ice water bath, was added 211 mg (1.88 mmoles) of potassium tert-butoxide. This mixture was subsequently stirred in the cold for fifteen minutes and then at room temperature for seven hours. The product was isolated by dilution of the mixture with 30 mL of 1:1 (v/v) ether:pentane and subsequent washing of the organic layer with 10% aqueous sodium chloride (3×30 mL). The organic layer was then dried over anhydrous sodium sulfate and filtered. Removal of the volatile organic solvents by evaporation at reduced pressure afforded 151 mg (62% yield) of bisacetal, shown by proton NMR analysis to be less pure than the bisacetal product obtained using hydroxide as the base in nonpolar organic solvents. Although use of potassium tert-butoxide as the base gave better results than the use of other alkoxide bases (Example XXIV), its higher cost (versus sodium or potassium hydroxide) and the formation of a larger amount of unidentified by-products render it less attractive for use in large-scale syntheses of the desired bisacetal.

EXAMPLE XXVI

Preparation of 2,7-Dimethyl-2,4,6-octatrienedial

A solution of 150 mg (0.585 mmole) of 1,1,8,8-tetramethoxy-2,7-dimethyl-2,4,6-octatriene, produced in accordance with Example XXV, in 3.5 mL of 4:2:1 (v/v/v) glacial acetic acid:tetrahydrofuran:water was heated at 45° C. (external oil bath temperature) for three hours. After cooling the solution to room temperature, the product was isolated by dilution of the mixture with 25 mL of 4:1 (v/v) ether:dichloromethane and washing the organic layer in successive order with saturated brine (2×25 mL), 4:1 (v/v) saturated brine:one molar aqueous sodium hydroxide (2×25 mL), and saturated brine (25 mL). The organic layer was then dried over anhydrous magnesium sulfate and filtered. Removal of the volatile organic solvents by evaporation at reduced pressure afforded 86 mg (90% yield) of the desired bisaldehyde, previously prepared in a similar manner by Pommer, et al., *Angew. Chem.*, 72, 911 (1960).

Although the foregoing detailed description has described the present invention by way of example, various changes and modifications to the exemplified procedures which have been illustrated herein may be practiced with the scope of the appended claims.

I claim:

1. A method for making 2,7-dimethyl-2,4,6-octatrienedial comprising the steps of:
    a) forming a first reaction mixture of
        i) X—CH$_2$—CH=CH—CH$_2$—X where X is chlorine or bromine, and
        ii) at least two equivalents of P(OR)$_3$ where R is C$_1$–C$_4$ alkyl;
    b) isolating 2-butenyl-1,4-bisphosphonic acid tetraalkyl ester from said first reaction mixture;
    c) forming a second reaction mixture at a temperature of about 0° C. or above in an essentially water-free, nonpolar organic solvent of
        i) 2-butenyl-1,4-bisphosphonic acid tetraalkyl ester,
        ii) at least two equivalents of CH$_3$—CO—CH=Z where —CH=Z is, selected from the group consisting of —CH(OR')$_2$, where R' is C$_1$–C$_4$ alkyl, and

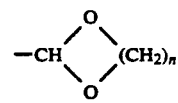

where n is an integer 2 or 3, and
        iii) at least two equivalents of a solid alkali metal hydroxide base;
    d) isolating

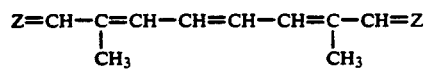

from said second reaction mixture;
    e) forming a third reaction mixture

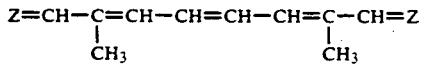

and water acidified to a pH of less than 4 to convert —CH=Z to an unprotected aldehyde; and f) isolating 2,7-dimethyl-2,4,6-octatrienedial from said third reaction mixture.

2. The method of claim 1 wherein X is chlorine.

3. The method of claim 1 wherein R is selected from the group consisting of ethyl and isopropyl.

4. The method of claim 1 wherein 2-butenyl-1,4-bisphosphonic acid tetraalkyl ester is 2-butenyl-1,4-bisphosphonic acid tetraethyl ester.

5. The method of claim 1 wherein said nonpolar organic solvent is selected from the group consisting of toluene, xylene, benzene, cyclohexane, hexane, heptane and mixtures thereof.

6. The method of claim 1 wherein said nonpolar organic solvent additionally comprises a cosolvent selected from the group consisting of diisopropylamine, diisopropyl ether, triethylamine, chlorobenzene and tetrahydrofuran.

7. The method of claim 6 wherein $R^1$ is methyl.

8. The method of claim 1 wherein said alkali metal hydroxide base is selected from the group consisting of potassium and sodium hydroxide.

9. The method of claim 8 wherein said alkali metal hydroxide base is sodium hydroxide.

10. The method of claim 1 wherein said second reaction mixture is formed at about room temperature.

11. The method of claim 1 wherein said third reaction mixture is a solution of
   i) glacial acetic acid,
   ii) tetrahydrofuran,
   iii) water, and
   iv) 1,1,8,8-tetramethoxy-2,7-dimethyl-2,4,6-octatriene.

12. The method of claim 1 wherein said second reaction mixture additionally comprises a drying agent.

13. The method of claim 12 wherein said drying agent is anhydrous potassium carbonate.

* * * * *